United States Patent [19]
Aust et al.

[11] Patent Number: 5,669,926
[45] Date of Patent: Sep. 23, 1997

[54] SURGICAL INSTRUMENT

[75] Inventors: Gilbert M. Aust, Huntsville; Timothy E. Taylor, Oxr, both of Ala.

[73] Assignee: Aust & Taylor Medical Corporation, Huntsville, Ala.

[21] Appl. No.: 686,571

[22] Filed: Jul. 26, 1996

Related U.S. Application Data

[63] Continuation-in-part of Ser. No. 8,670, Jan. 25, 1993, Pat. No. 5,540,706.

[51] Int. Cl.$^6$ .................................................. A61B 17/32
[52] U.S. Cl. ................................................ 606/170; 606/180
[58] Field of Search .................................. 606/170, 167, 606/174, 175, 177, 180

[56] References Cited

U.S. PATENT DOCUMENTS

| | | | |
|---|---|---|---|
| 4,274,414 | 6/1981 | Johnson et al. | 606/170 |
| 4,362,160 | 12/1982 | Hiltebrandt | 606/170 |
| 4,499,899 | 2/1985 | Lyons, III . | |
| 4,517,977 | 5/1985 | Frost . | |
| 4,649,919 | 3/1987 | Thimsen et al. . | |
| 4,763,669 | 8/1988 | Jaeger . | |
| 4,834,069 | 5/1989 | Umeda . | |
| 4,834,729 | 5/1989 | Sjostrom . | |
| 5,025,804 | 6/1991 | Kondo . | |
| 5,100,426 | 3/1992 | Nixon . | |
| 5,143,475 | 9/1992 | Chikama . | |
| 5,178,129 | 1/1993 | Chikama et al. . | |
| 5,354,311 | 10/1994 | Kambin et al. . | |

*Primary Examiner*—Michael Buiz
*Assistant Examiner*—Kevin Truong
*Attorney, Agent, or Firm*—Tarolli, Sundheim, Covell Tummino & Szabo

[57] ABSTRACT

A surgical instrument comprises a manually engageable handle. A first stem section having a longitudinal axis extends from the handle. A second stem section is connected between the first stem section and a cutting tool. The cutting tool includes a rotatable shaver. The second stem section has at least a portion which is bendable. A rotatable drive shaft is connected with the shaver and extends axially through the first stem section and the second stem section. The drive shaft has a flexible portion disposed in the flexible stem section. A passage extends axially through the drive shaft for conducting tissue from a location adjacent to the cutting tool through the second stem section toward the handle. A mechanism is connected to the bendable portion of the second stem section for bending the bendable portion to change the orientation of the cutting tool relative to the axis and to the first stem section from a first orientation to a second orientation. The bendable portion of the second stem section includes mechanism for enabling bending movement of the bendable portion by the mechanism to locate the cutting tool at the same angle relative to the longitudinal axis of the first stem section at more than one location along the length of the bendable portion.

17 Claims, 4 Drawing Sheets

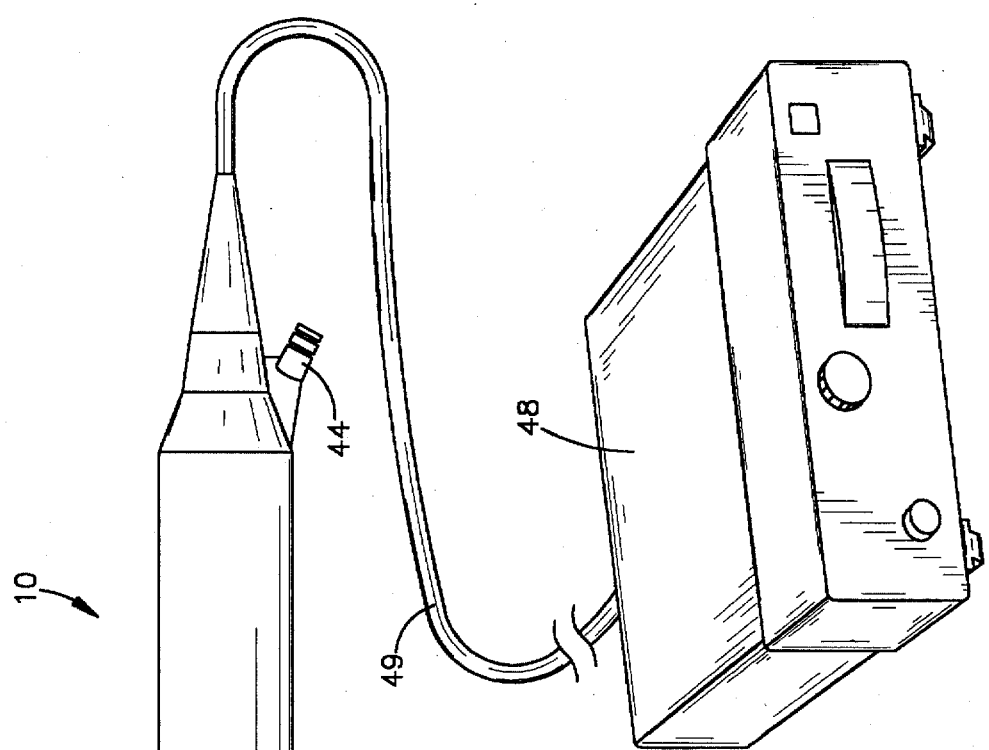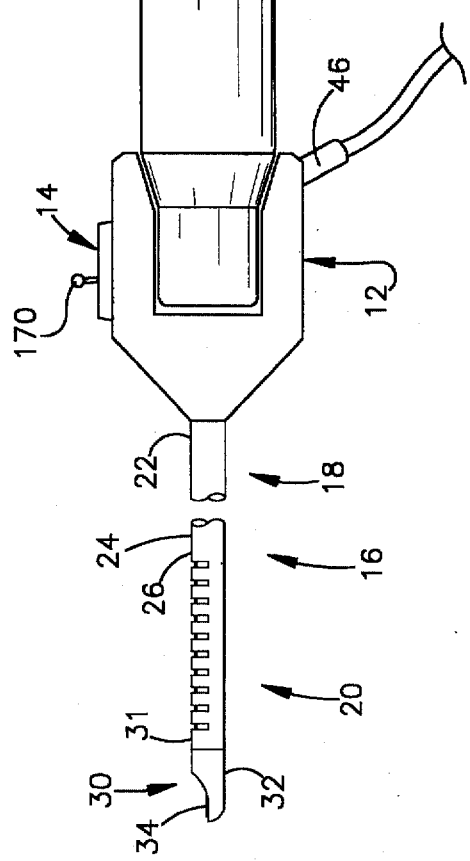
Fig.1

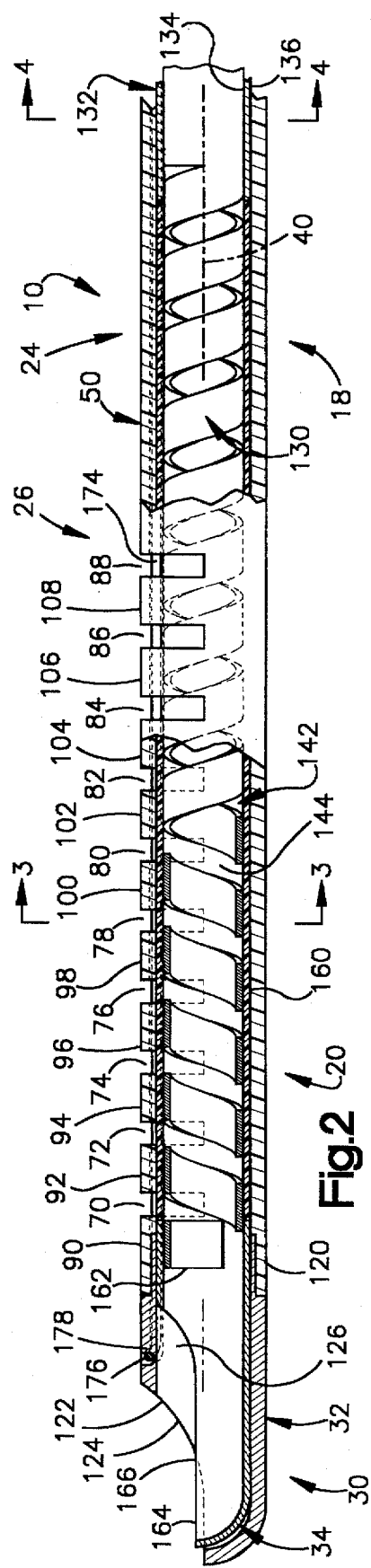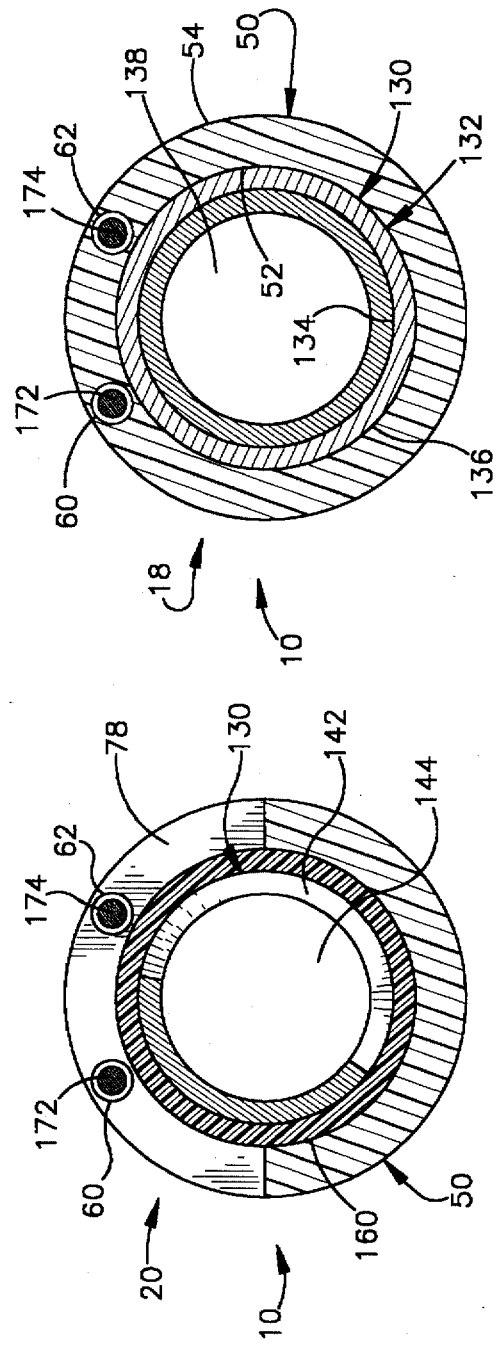

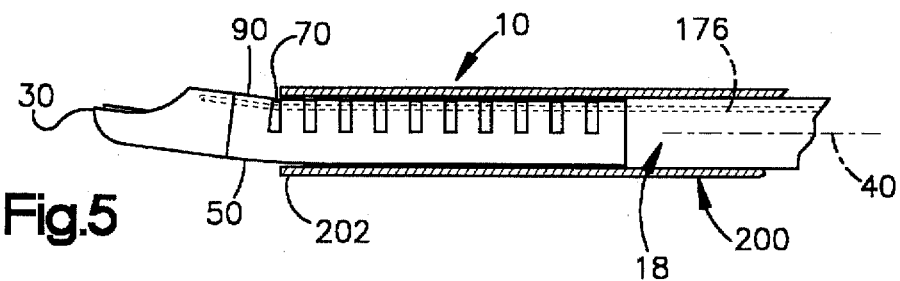
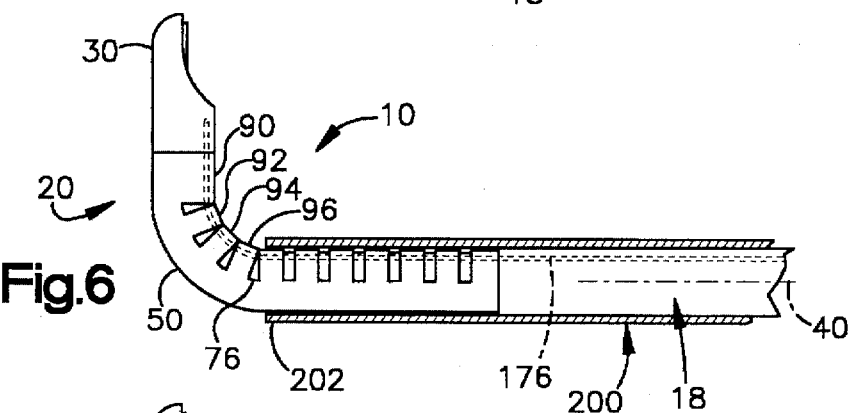
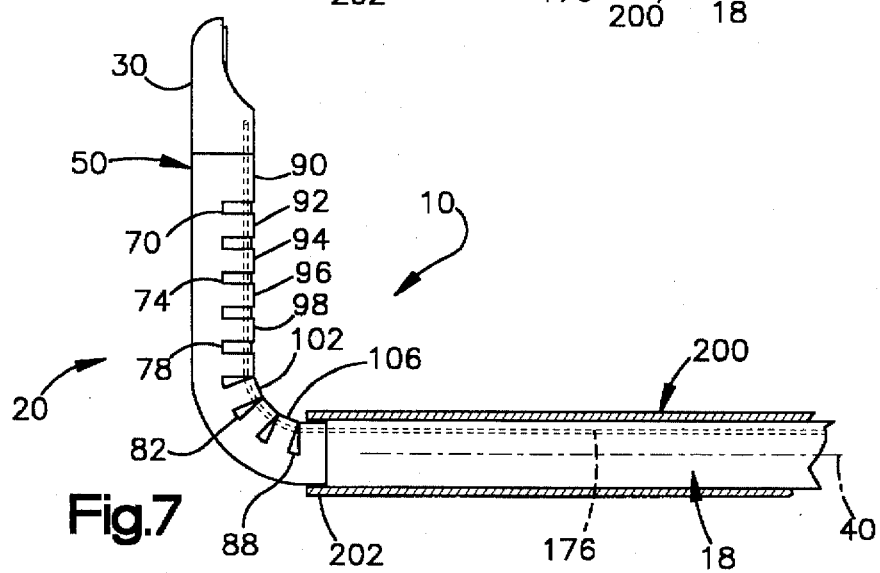
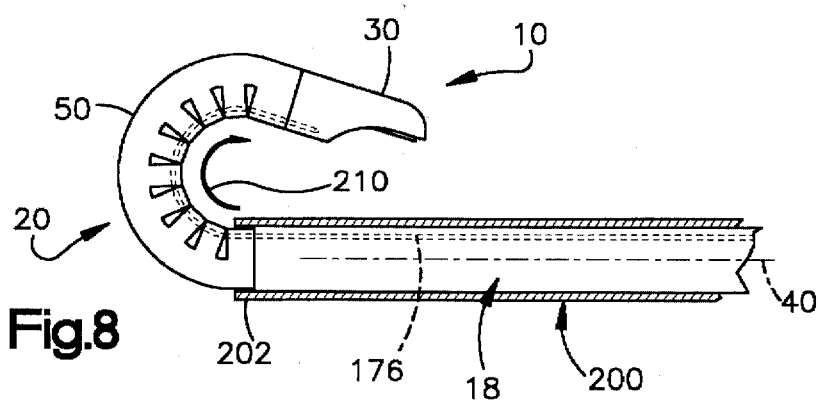

SURGICAL INSTRUMENT

RELATED APPLICATION

This application is a continuation-in-part of U.S. patent application Ser. No. 08/008,670, filed Jan. 25, 1993, now U.S. Pat. No. 5,540,706, dated Jul. 30, 1996, by the same inventors and entitled SURGICAL INSTRUMENT.

BACKGROUND OF THE INVENTION

The present invention relates to a surgical instrument for removing tissue such as tissue from a human body. In particular, the present invention relates to a surgical instrument which has a rotatable cutting tool, is steerable, and provides suction for removing tissue which is cut. The instrument may be used, for example, in operations involving a spinal disc.

SUMMARY OF THE INVENTION

The present invention is a surgical instrument comprising a manually engageable handle. A first stem section having a longitudinal axis extends from the handle. A second stem section is connected between the first stem section and a cutting tool. The cutting tool includes a rotatable cutter. The second stem section has at least a portion which is bendable. A rotatable drive shaft is connected with the cutter and extends axially through the first stem section and the second stem section. The drive shaft has a flexible portion disposed in the flexible stem section. A passage extends axially through the drive shaft for conducting tissue from a location adjacent to the cutting tool through the second stem section toward the handle. A mechanism is connected to the bendable portion of the second stem section for bending the bendable portion to change the orientation of the cutting tool relative to the axis and to the first stem section from a first orientation to a second orientation. The bendable portion of the second stem section includes means for enabling bending movement of the bendable portion by the mechanism to locate the cutting tool at the same angle relative to the longitudinal axis of the first stem section at more than one location along the length of the bendable portion.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is an illustration of a surgical instrument constructed in accordance with the present invention;

FIG. 2 is an enlarged sectional view of a portion of the surgical instrument of FIG. 1;

FIG. 3 is a sectional view taken along line 3—3 of FIG. 2;

FIG. 4 is a sectional view taken along line 4—4 of FIG. 2;

FIGS. 5–8 are a series of views illustrating a portion of the surgical instrument of FIG. 1 shown in different positions.

DESCRIPTION OF PREFERRED EMBODIMENTS

Figure 9:
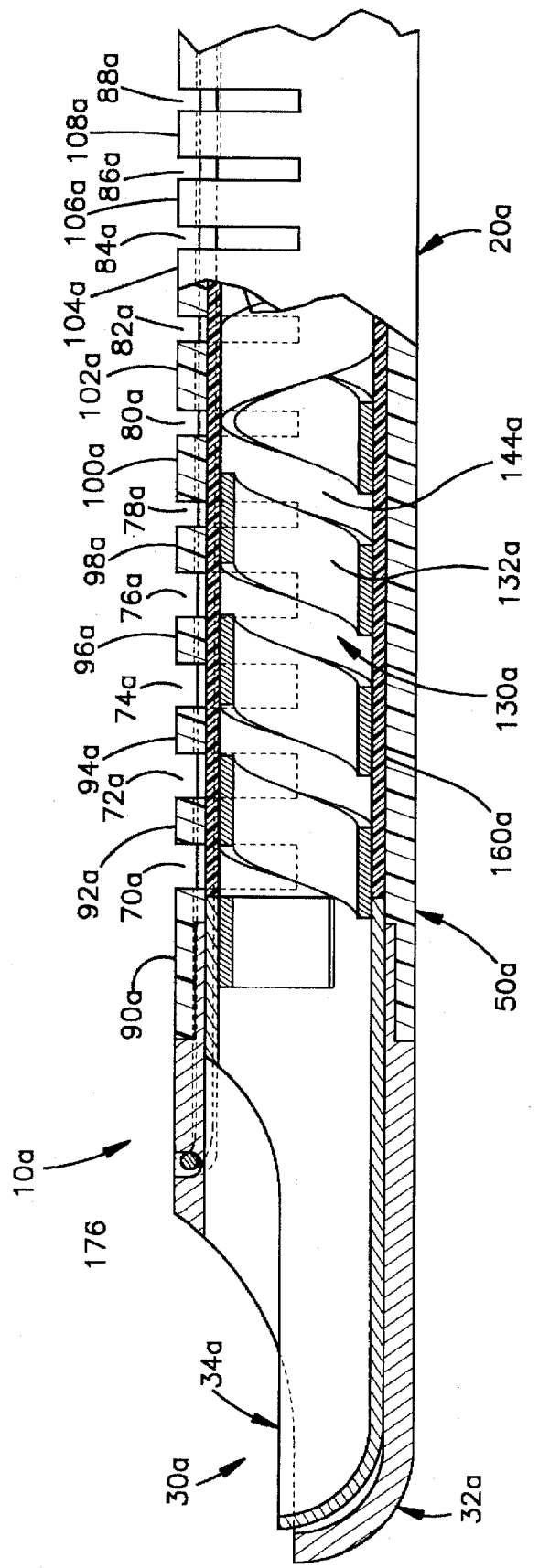
FIG. 9 is a view similar to FIG. 2 of a portion of a surgical instrument constructed in accordance with a second embodiment of the present invention.

FIGS. 1–8 illustrate a surgical instrument 10 which is constructed in accordance with a first embodiment of the present invention. The surgical instrument 10 includes a handle 12 and an actuator assembly 14. A stem section 16 is connected with and projects from the handle 12. The stem section 16 includes a first stem section 18 and a second stem section 20.

A proximal end portion 22 of the first stem section 18 is fixed to the handle 12. A proximal end portion 24 of the second stem section 20 is connected with a distal end portion 26 of the first stem section 18. A rotary cutter assembly or shaver assembly 30 is connected with a distal end portion 31 of the second stem section 20. The shaver assembly 30 includes a fixed outer part 32 and a rotatable inner part 34.

The first stem section 18 is constructed so as to be substantially rigid, or non-bendable, during use of the surgical instrument 10. The rigid stem section 18 has a longitudinal central axis 40 (FIG. 2) which forms a longitudinal central axis of the surgical instrument 10. The second stem section 20 is constructed to be bendable during use of the surgical instrument 10. The actuator assembly 14 is manually operable, in a manner described below, to bend the bendable stem section 20 to move the shaver assembly 30 between any one of many positions off the axis 40 relative to the rigid stem section 18.

A suction pump (not shown) is preferably connected with the handle 12 at a connection indicated at 44 (FIG. 1). A source of water or other irrigation fluid (not shown) is preferably connected with the handle 12 at a connection indicated at 46 in FIG. 1. A control apparatus 48 is connected with the surgical instrument 10 through a cord system 49.

The stem section 16 (FIGS. 2–4) of the surgical instrument 10 includes a main body portion 50. The main body portion 50 is fixedly secured to the handle 12. The main body portion 50 is made from a resilient plastic material, preferably Silastic (TRADEMARK) brand plastic available from Dow Corning Corporation. The main body portion 50 of the surgical instrument 10 has a tubular, cylindrical configuration including parallel inner and outer surfaces 52 and 54. The main body portion 50 extends along the length of both the rigid stem section 18 and the bendable stem section 20.

A pair of cylindrical deflection control wire passages 60 and 62 are formed in the main body portion 50. The passages 60 and 62 extend parallel to each other and to the axis 40. The passages 60 and 62 extend along the length of the rigid stem section 18 and along the length of the bendable stem section 20.

The main body portion 50 of the instrument 10 is selectively slotted or relieved, along at least a portion, and preferably all, of the length of the bendable stem section 20, to lower the bending resistance of the second stem section in a predetermined manner. In the illustrated embodiment, a series of ten openings or slots 70, 72, 74, 76, 78, 80, 82, 84, 86 and 88 are formed in the upper (as viewed in FIGS. 2 and 3) sector of the main body portion 50. Each one of the slots 70–88 has a circumferential extent of about 180°.

The slots 70–88 define a series of ten relatively movable links 90, 92, 94, 96, 98, 100, 102, 104, 106 and 108. The links 90–108 are the sections of the main body portion 50 which are located axially between adjacent slots 70–88. The slots 70–88 act as pivot joints or pivot axes between the links 90–108. The links 90–108 are pivotally interconnected by the material of the main body portion 50 which is not cut away at the slots 70–88. The links 90–108 enable controlled movement of the shaver assembly 30 to a plurality of positions off the axis 40 as illustrated, for example, in FIGS. 5–8.

In the embodiment illustrated in FIGS. 1–8, the axially-measured distance between each pair of adjacent slots 70–88 is predetermined and is uniform. Thus, the bending resistance of the main body portion 50, resulting from slot placement, is uniform along the length of the bendable stem section 20 of the surgical instrument 10. Further, the width (or axial extent) of each one of the slots 70–88 is uniform along the length of the bendable stem section 20. Thus, the bending resistance of the main body portion 50, resulting from slot width, is uniform along the length of the bendable stem section 20 of the surgical instrument 10.

The outer part 32 of the shaver assembly 30 is fixedly secured in a known manner, such as by bonding, to a distal end portion 120 of the main body portion 50 of the instrument 10. The outer part 32 of the shaver assembly 30 has a generally cylindrical, tubular configuration with a tissue opening 122 defined by a first cutting edge 124. The tissue opening 122 communicates with a central chamber 126 in the outer part 32 of the shaver assembly 30. The shaver assembly 30 is preferably made from metal and may be constructed in a manner similar to that disclosed in U.S. Pat. No. 4,598,710.

A rotatable drive shaft 130 is disposed radially inward of the main body portion 50 of the surgical instrument 10. A rigid portion 132 of the drive shaft 130 is disposed within the rigid stem section 18. The rigid portion 132 of the drive shaft 130 is a cylindrical metal tube which has parallel cylindrical inner and outer surfaces 134 and 136.

The inner surface 134 of the rigid portion 132 of the drive shaft 130 defines a central passage 138 of the rigid stem section 18. The rigid portion 132 of the drive shaft 130 is connected with the drive shaft (not shown) of a suitable electric motor in the handle 12 and is rotatable about the longitudinal central axis 40 by operation of the motor.

A flexible portion 142 of the drive shaft 130 is disposed within the bendable portion of the main body portion 50 of the main body portion 50 of the surgical instrument 10. The flexible portion 142 of the drive shaft 130 is preferably formed as a helical coil spring, preferably made from metal having a rectangular cross-sectional configuration, but could alternatively be formed in a different manner. The flexible portion 142 of the drive shaft 130 is capable of transmitting rotational force from the rigid portion 132 of the drive shaft to the rotatable inner part 34 of the shaver assembly 30. The flexible portion 142 of the drive shaft 130 has an axially extending, central passage 144.

The flexible portion 142 of the drive shaft 132 also provides a self-centering effect for the bendable stem section 20 of the surgical instrument 10. Specifically, when the bendable stem section 20 of the instrument 10 is bent to a condition off the axis 40, as described below, the resilience provided by the spring configuration of the flexible portion 124 of the drive shaft 130 returns the bendable stem section 20 to its linear position upon release of the bending force. The tubular plastic main body portion 50 also has a self-centering effect.

A plastic inner sheath 160 in the form of a shrink wrap overlies the flexible portion 142 of the drive shaft 132. The sheath 160 seals the openings between adjacent turns of the coil spring drive shaft 142. The sheath 160 is, for clarity, shown with an exaggerated thickness in FIGS. 2 and 3.

The rotatable inner part 34 of the shaver assembly 30 is secured to a distal end 162 of the flexible portion 142 of the drive shaft 130. The inner part 34 of the shaver assembly 30 has a generally cylindrical configuration and is rotatable within the central chamber 126 in the outer part 32 of the shaver assembly. The inner part 34 of the shaver assembly 30 has a tissue opening 164 defined by a second cutting edge 166. The tissue opening 164 in the inner part 34 of the shaver assembly 30 communicates with the central passage 144 in the flexible portion 142 of the drive shaft 130.

During use of the surgical instrument 10, it is preferable to convey away from the shaver assembly 30 tissue which is removed from between vertebra or other locations. Accordingly, a suction pump (not shown) is connected with the instrument handle 10 at the connection 44. Suction is applied to the shaver assembly 30 through the central passage 138 in the rigid stem section 18 and through the central passage 144 in the bendable stem section 20.

Upon rotation of the drive shaft 130, the second cutting edge 166 on the inner part 34 of the shaver assembly 30 cooperates with the first cutting edge 124 on the outer part 32 of the shaver assembly, in a known manner, to remove tissue. The removed tissue is drawn into the central chamber 126 of the shaver assembly 30 by suction applied through the central passage 138 of the rigid stem section 18 and through the central passage 144 of the flexible portion 142 of the drive shaft 130. The suction draws or pulls tissue from the area immediately adjacent to the shaver assembly 30 back through the center of the flexible portion 142 of the drive shaft 130 and through the center of the rigid portion 132 of the drive shaft, to the connection 44 and the suction conduit.

In addition, water or other fluid can be utilized to irrigate the area where tissue is removed by the shaver assembly 30. The irrigation fluid is conducted through the central passage 138 in the rigid stem section 18 and through the central passage 144 in the bendable stem section 20, to the shaver assembly 30.

Other known types of rotatable tissue cutting devices may be substituted for the shaver assembly 30. Thus, a generally spherical rotatable burr or router may be used to abrade tissue. The particular type of shaver or shaver assembly which is connected with the bendable stem section 20 will depend upon the surgical operation to be performed.

The actuator assembly 14 of the surgical instrument includes a deflection control lever 170 (FIG. 1) which projects from the handle 12. The deflection control lever 170 is supported for pivotal movement relative to the handle 12. A spring (not shown) or other device, connected between the deflection control lever 170 and the handle 12, biases the deflection control lever into the unactuated position shown in FIG. 1.

The actuator assembly 14 also includes two deflection control wires 172 and 174. The wires 172 and 174 are preferably separate portions of a single loop of wire 176 which has its proximal ends connected for movement with the deflection control lever 170. The deflection control wires 172 and 174 extend from the deflection control lever 170 through the deflection control wire passages 60 and 62, respectively, in the main body portion 50.

The deflection control wires 172 and 174 are connected in a force-transmitting relationship with the fixed portion 32 of the shaver assembly 30. Specifically, the wires 172 and 174 loop around a fixed portion 178 of the shaver assembly 30. As a result, tensile forces on the wires 172 and 174, resulting from movement of the actuator control lever 170, are transmitted to the shaver assembly 30.

The surgical instrument 10 is typically used in association with a cannula 200 (FIGS. 5–8) having an open distal end 202. The cannula 200 is a known tubular member of any suitable construction which is used, in a known manner, to provide an open path through body tissue to the operating site. Once the cannula 200 is properly positioned, the surgical instrument 10 is inserted axially through the cannula until at least the shaver assembly 30 protrudes from the distal end 202 of the cannula 200. A predetermined amount of the bendable stem section 20 of the surgical instrument 10 may also protrude from the distal end 202 of the cannula 200, as described below.

When the surgical instrument 10 is thus inserted through the cannula 200, and the deflection control lever 170 is moved, the second stem section 20 of the surgical instrument is bendable at about the location of the distal end 202 of the cannula 200, to position the shaver assembly 30 in the desired location.

Specifically, the actuation control lever 170 is pivoted relative to the handle 12 so as tension the deflection control wires 172 and 174. Tension in the wires 172 and 174 is effective to pivot the bendable stem section 20 of the instrument in a clockwise direction as viewed in FIGS. 5–8. The shaver assembly 30 is pulled in a clockwise direction (as viewed in FIGS. 5–8) from the linear position shown in FIG. 2 toward the position shown in FIG. 8. As this occurs, one or more of the links 90–108 of the bendable stem section 20 pivot about one or more of the slots or pivot axes 70–88.

The distal end portion 602 of the cannula 200 acts as a fulcrum about which the surgical instrument 10 bends. The surgical instrument 10 bends at different locations along its length, depending on how much of the surgical instrument protrudes from the distal end 202 of the cannula 200. The surgical instrument 10 bends at different locations along the length of the bendable stem section 20 because of the restrictions on its movement resulting from the presence of the cannula 200. Thus, the bendable stem section 20 of a surgical instrument 10, in accordance with the present invention, can be bent at the same angle relative to the longitudinal axis 40 at more than one location along the length of the bendable stem section 20. For example, as shown in FIG. 6, if only the four most distally located links 90, 92, 94 and 96 of the bendable stem section 20 protrude from the distal end 202 of the cannula 200, the surgical instrument 10 bends at the approximate location of the pivot axis 76. The shaver assembly 30 as shown in FIG. 6 extends at an angle of 90° to the central axis 40, at the approximate location of the slot or pivot axis 72.

In another example, if all of the links 90–108 protrude from the distal end 202 of the cannula 200, the surgical instrument 10 bends in a manner as shown in FIG. 7. The presence of the cannula 200 causes the bendable stem section 20 of the surgical instrument 10 to bend at the approximate location of the most proximal pivot axis or slot 88. The shaver assembly 30 in FIG. 7 extends at an angle of 90° to the central axis 40, at the approximate location of the pivot axis 88. This location is spaced apart from the bending location shown in FIG. 6 by a substantial distance along the length of the bendable stem section 20 of the surgical instrument 10.

Thus, the positioning of the surgical instrument 10 relative to the cannula 200 can control and determine the bending location. It should be noted that, instead of a cannula, the wall of a body space can be used to control the bending. For example, the tough outer wall of a spinal disc can act as the fulcrum for bending the surgical instrument 10 to perform work within the spinal disc.

Further, the bendable stem section 20 of the surgical instrument 10 can bend up to 90° to 180°, or more, at almost any location along its length depending on the range of pivotal movement which is available at each pivot axis 70–88.

For example, the bendable stem section 20 might be independently bendable by, for example, 18° at each of ten different locations along the length of the bendable stem section, thus providing a total of 180° of bending movement. As another example, the bendable stem section 20 is shown in FIG. 8 bent through an arc 210 which has a circumferential extent of greater than 180°. The amount of bending of the bendable stem section 20 of the surgical instrument 10 is controlled by the amount of tension on the deflection control wires 172 and 174 and by the amount of movement of the deflection control lever 170.

Because of the ability of the surgical instrument 10 to bend at 90° or more at almost any selected location along the length of the bendable stem section 20, the shaver assembly 30 can be positioned and used in substantially any position outside the distal end 202 of the cannula 200. This is enhanced by the fact that no portions of the surgical instrument 10 extend radially outward of the links 90–108 and so the surgical instrument can be "pistoned" or moved axially with little restriction even when the bendable stem section 20 is bent at 90° or more. These features provide a much larger operating field than is available with a surgical instrument which bends to 90° at only one location along its length.

The actuator assembly 14 can thus be operated to change the orientation of the shaver assembly 30 relative to the rigid portion 18 of the stem section 16 and relative to body tissue during an operation. The actuator assembly 14 can be operated to positively change the orientation of the shaver assembly 30 through a range of 180° from the straight initial orientation. The drive shaft 130 and the inner shaver part 134 are rotatable to effect tissue removal while the bendable stem section 20 is in any orientation. In addition, the bendable stem section 20 can be deflected or bent under the influence of forces applied to the shaver assembly 30, relative to the straight initial orientation shown in FIG. 2.

Devices constructed in accordance with the present invention which exhibit uniform bending resistance along the length of the bendable stem section 20 bend in one manner only when bent in free space (for example, as viewed in FIG. 6). In this case, a cannula or a wall of a body space, for example, is used to restrict and control the movement of the bendable stem section 20 of the device 10.

In contrast, devices constructed in accordance with the present invention which are non-uniform along their length, that is, which have features to selectively vary the bending resistance along their length, can bend at different locations along their length even when bent in free space. In this case, a cannula or a wall of a body space, for example, may not be necessary to restrict and control the movement of the bendable stem section 20 of the device. Such devices include the surgical instrument 10a, a portion of which is illustrated in FIG. 9. The surgical instrument 10a is identical to the surgical instrument 10 (FIGS. 1–8) with the exception of the placement and width of the slots in the main body portion. Thus, parts of the surgical instrument 10a (FIG. 9) which are the same as, or similar to, corresponding parts of the surgical instrument 10 (FIGS. 1–8) are given the same reference numeral with the suffix "a" attached.

In the surgical instrument 10a (FIG. 9), the distance between adjacent pairs of slots 70a–88a in the main body portion 50a along the length of the bendable stem section 20a varies, to vary the bending resistance of the main body portion and thus of the bendable stem section of the surgical instrument.

For example, the slots 78a–84a are spaced apart by a first distance along the length of the bendable stem section 20a of the surgical instrument 10a. The first distance is relatively large. This tends to increase the bending resistance of the main body portion 50a, and thus of the bendable stem section 20a, at the location of the slots 78a–84a, because the slots are relatively far apart. In contrast, the slots 84a–88a are spaced apart by a second distance along the length of the bendable stem section 20a of the surgical instrument 10a. The second distance is substantially less than the first distance. This tends to decrease the bending resistance of the main body portion 50a, at the location of the slots 84a–88a to a level which is less than the bending resistance at the location of the slots 78a–84a.

Further, the width (or axial extent) of at least some of the slots 70a–88a on the main body portion 50a of the surgical instrument 10a varies, from slot to slot, along the length of the bendable stem section 20a. For example, the width of the slots 70a–76a is relatively great compared to the width of the slots 78a–88a. This tends to lower the bending resistance of the main body portion 50a, and thus of the bendable stem section 20a of the surgical instrument 10a, at the location of the slots 70a–76a.

From the above description of the invention, those skilled in the art will perceive improvements, changes and modifications in the invention. Such improvements, changes and modifications within the skill of the art are intended to be covered by the appended claims.

Having described the invention, we claim:

1. A surgical instrument comprising:

a manually engageable handle;

a first stem section having a longitudinal axis and extending from said handle;

a cutting tool including a rotatable shaver;

a second stem section connected between said first stem section and said cutting tool, said second stem section having at least a portion which is bendable;

a rotatable drive shaft connected with said shaver and extending axially through said first stem section and said second stem section, said drive shaft having a flexible portion disposed in said bendable portion of said second stem section;

a passage extending axially through said drive shaft for conducting tissue from a location adjacent to said cutting tool through said second stem section toward said handle; and a mechanism connected to said bendable portion of said second stem section for bending said bendable portion to change the orientation of said cutting tool relative to said axis and to said first stem section from a first orientation to a second orientation;

said bendable portion of said second stem section comprising means for enabling bending movement of said bendable portion by said mechanism to locate said cutting tool at the same angle relative to said longitudinal axis of said first stem section at more than one location along the length of said bendable portion.

2. A surgical instrument as set forth in claim 1 wherein said bendable portion of said second stem section comprises means for enabling bending movement of said bendable portion by said mechanism to locate said cutting tool at an angle of 90° relative to said longitudinal axis of said first stem section at more than one location along the length of said bendable portion.

3. A surgical instrument as set forth in claim 1 wherein said bendable portion of said second stem section comprises a tubular plastic body portion, said means for enabling bending movement comprising a series of openings formed in said tubular plastic body portion and defining in said tubular plastic body portion a series of pivotally interconnected links disposed along the length of said bendable portion of said second stem section, said flexible portion of said drive shaft being disposed within said links.

4. A surgical instrument as set forth in claim 3 wherein said openings comprise slots which extend circumferentially at least partially around said plastic body portion.

5. A surgical instrument as set forth in claim 1 wherein said mechanism for bending comprises an actuator on said handle and at least one deflection control wire which is disposed radially outward of said suction passage and which is connected in a force-transmitting relationship between said actuator and a distal end portion of said surgical instrument for transmitting bending force from said actuator to said distal end portion of said surgical instrument to cause bending movement of said bendable portion of said second stem section.

6. A surgical instrument as set forth in claim 1 in combination with a cannula through which said instrument is extensible, said bendable portion of said second stem section projecting from said cannula when in use, said instrument bending at the distal end of said cannula when force is applied by said means for bending.

7. A surgical instrument as set forth in claim 1 wherein said flexible drive shaft comprises a coil spring extending through said bendable portion of said second stem section.

8. A surgical instrument as set forth in claim 7 wherein said coil spring is made from an elongate metal member having a rectangular cross-sectional configuration.

9. A surgical instrument as set forth in claim 7 wherein said suction passage extends axially through said bendable portion of said drive shaft for conducting tissue from a location adjacent to said cutting tool through said second stem section toward said handle.

10. A surgical instrument as set forth in claim 1 comprising a series of links having predetermined different lengths along the length of said bendable portion of said second stem section to vary the bending resistance of a tubular plastic body portion.

11. A surgical instrument as set forth in claim 10 comprising a series of openings separating and defining said links, said series of openings including at least a first set of openings having a first configuration for providing a first degree of bending resistance at the location of said first set of openings and a second set of openings having a second configuration different from said first configuration for providing a second degree of bending resistance at the location of said second set of openings, said second degree of bending resistance being greater than said first degree of bending resistance.

12. A surgical instrument as set forth in claim 11 wherein each one of said first set of openings has a first predetermined extent along the length of said bendable portion of said second stem section and each one of said second set of openings has a second predetermined extent along the length of said bendable portion of said second stem section which is less than said first predetermined extent.

13. A surgical instrument as set forth in claim 1 wherein said means for enabling bending movement comprises means for selectively providing a predetermined first degree of bending resistance of said bendable portion at a first location along the length of said bendable portion and for selectively providing a predetermined second degree of bending resistance of said bendable portion at a second location along the length of said bendable portion, said second degree of bending resistance being greater than said first degree of bending resistance.

14. A surgical instrument comprising:

a manually engageable handle;

a plastic body portion, said plastic body portion including a rigid section having a longitudinal axis and extending from said handle, said plastic body portion including a bendable section extending from said rigid section;

a series of openings formed in said bendable section of said plastic body portion and defining in said bendable section a series of pivotally interconnected links disposed along the length of said bendable section;

a cutting tool including a rotatable shaver;

a rotatable drive shaft connected with said shaver and extending axially through said plastic body portion, said drive shaft having a flexible portion disposed in said bendable section of said plastic body portion;

a passage extending axially through said flexible portion of said drive shaft for conducting tissue from a location adjacent to said cutting tool through said bendable section toward said handle; and a mechanism connected to said bendable section for bending said bendable section to change the orientation of said cutting tool relative to said axis from a first orientation to a second orientation;

said bendable section being bendable by said mechanism to locate said cutting tool at the same angle relative to said longitudinal axis at more than one location along the length of said bendable section.

15. A surgical instrument as set forth in claim 14 wherein said cutting tool includes a non-rotatable part fixed to a distal end of said plastic body portion of said surgical instrument, said rotatable shaver being supported for rotation relative to said non-rotatable part.

16. A surgical instrument as set forth in claim 14 wherein said openings are slots which extend around a portion of the circumference of said tubular plastic body portion.

17. A surgical instrument as set forth in claim 14 wherein said bendable section of said plastic body portion comprises means for enabling bending movement of said bendable portion by said mechanism to locate said cutting tool at an angle of 90° relative to said longitudinal axis of said first stem section at more than one location along the length of said bendable section.

* * * * *